(12) United States Patent
Muller et al.

(10) Patent No.: US 7,167,540 B2
(45) Date of Patent: Jan. 23, 2007

(54) DEVICE FOR IRRADIATING TISSUE

(76) Inventors: Reinhold G. Muller, Ringstrasse 12, Marloffstein 91080 (DE); Nils Achterberg, Kapellenstrasse 6, Neunkirchen am Sand 91233 (DE)

(*) Notice: Subject to any disclaimer, the term of this patent is extended or adjusted under 35 U.S.C. 154(b) by 0 days.

(21) Appl. No.: 10/362,106

(22) PCT Filed: Aug. 18, 2001

(86) PCT No.: PCT/DE01/03167

§ 371 (c)(1),
(2), (4) Date: Jul. 23, 2003

(87) PCT Pub. No.: WO02/15975

PCT Pub. Date: Feb. 28, 2002

(65) Prior Publication Data

US 2004/0044265 A1 Mar. 4, 2004

(30) Foreign Application Priority Data

Aug. 24, 2000 (DE) .................. 100 41 473

(51) Int. Cl.
*A61N 5/10* (2006.01)
(52) U.S. Cl. ...................................... 378/65
(58) Field of Classification Search .............. 378/64, 378/65, 124, 137; 250/492.1, 494.1
See application file for complete search history.

(56) References Cited

U.S. PATENT DOCUMENTS

| 2,741,704 | A | * | 4/1956 | Trump et al. ............ 250/492.3 |
| 2,931,941 | A | | 4/1960 | Dewey, II et al. |
| 3,349,242 | A | * | 10/1967 | Braestrup .................... 378/65 |
| 4,998,268 | A | * | 3/1991 | Winter ........................ 378/65 |
| 5,321,271 | A | | 6/1994 | Schonberg et al. |
| 5,433,693 | A | | 7/1995 | Ott |
| 5,764,723 | A | * | 6/1998 | Weinberger et al. .......... 378/65 |

(Continued)

FOREIGN PATENT DOCUMENTS

| DE | 27 30 985 C2 | 1/1978 |
| DE | 196 04 789 A1 | 8/1997 |

(Continued)

OTHER PUBLICATIONS

XP-001032074 "A proposed therapy at the SSC", B.A. Prichard, Jr., Nuclear Instruments and Methods in Physics Reseacrh B79 (1993) 895-897 North Holland.

(Continued)

*Primary Examiner*—Edward J. Glick
*Assistant Examiner*—Chih-Cheng Glen Kao
(74) *Attorney, Agent, or Firm*—Merchant & Gould P.C.

(57) ABSTRACT

The invention relates to a device (1) for irradiating tissue, especially tumors. The device comprises one radiation source (2) (accelerator), the primary radiation (6) thereof leading to at least one radiation head (3). The radiation source (2) and radiation head (3) are arranged in a housing and the radiation emitted from the radiation head (3) hits the tissue. A plurality of radiation heads (3) are arranged in a fixed manner in the housing.

11 Claims, 2 Drawing Sheets

U.S. PATENT DOCUMENTS

Figure 1:
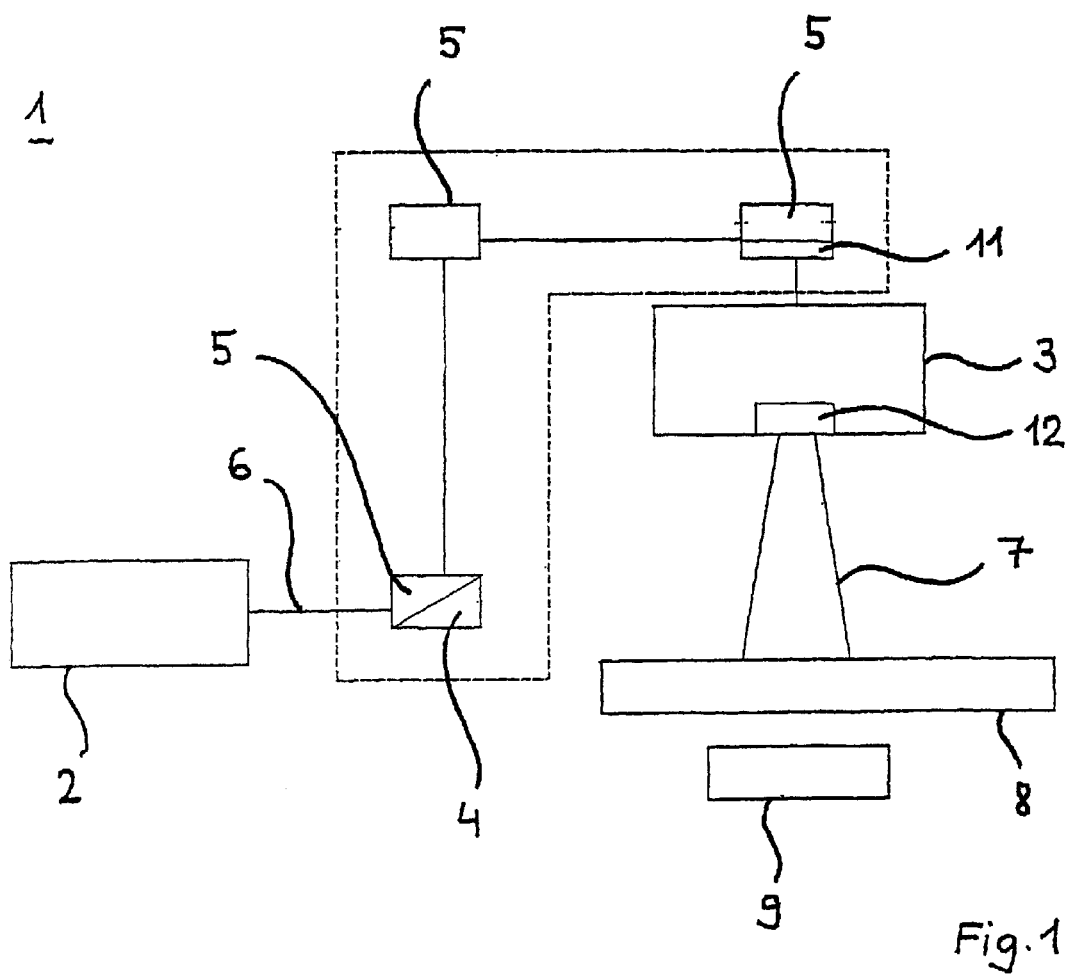

| | | | |
|---|---|---|---|
| 5,847,401 A * | 12/1998 | McKeown et al. | 250/492.3 |
| 6,049,587 A | 4/2000 | Leksell et al. | |
| 6,060,833 A * | 5/2000 | Velazco | 315/5.41 |
| 6,504,898 B1 * | 1/2003 | Kotler et al. | 378/64 |

FOREIGN PATENT DOCUMENTS

| | | |
|---|---|---|
| DE | 196 50 013 A1 | 6/1998 |
| DE | 197 36 192 C2 | 3/1999 |
| EP | 0 382 560 A1 | 8/1990 |

OTHER PUBLICATIONS

XP-002188971 "Selection of beam angles for radiotherapy of skull bae tumours using charged particles", Jakel O. and Debus J., Phys. Med. Biol. 45 (2000) 1229-1241.

XP-000895556 "Design of a beam transport system for a protein radiation therapy facility", W.P. Jones and G.P.A. Berg, Proceedings of the 1999 Particle Accelerator Conference, New York, 1999, 2519-2521.

* cited by examiner

DEVICE FOR IRRADIATING TISSUE

The invention relates to a device for irradiating tissue, especially tumors, with at least one radiation source, whose primary beam leads to at least one radiation head, the radiation source and the radiation head being arranged in a housing and the radiation released by the radiation head striking the tissue.

With the realization of intensity-modulated radiation therapy, new treatment processes become possible. A very promising concept is the so-called tomotherapy, which represents the most comprehensive attempt at optimization of percutaneous (effective through the skin) tumor therapy with ionizing radiation. Tumor-conforming irradiation is achieved through special devices, especially collimators, for intensity modulation and for restricting the photon beam to the target volume.

For irradiation, the patient is pushed on a patient table into a therapy apparatus in which, through rotation of the gantry, a multiplicity of irradiation directions can be set. The radiation generated by a radiation source is guided to one or several radiation heads. As with the classical sectional-image CT, the radiation head rotates around the patient and radiates the tissue to be treated layer by layer. Through appropriate control of the collimator the desired dosage distribution in the patient can be achieved. In a manner analogous to the spiral CT, the patient can also be moved relative to the radiation head. Here the radiation beam describes a spiral path around the patient. The disadvantage of the known devices consists in the high technological costs associated with precise rotation of heavy masses as well as the problematic energy and information transfer with rotating systems. Thus, there arise, for example, waiting times until a change can be made from one beam direction to the next.

The object of the invention is therefore to further develop a device for irradiation of tissue, especially tumors, with at least one radiation source, whose primary beam leads to at least one radiation head, the radiation source and the radiation head being arranged in a housing and the radiation released by the radiation head striking the tissue, such that technical reliability is increased while using simple construction and that the costs associated with radiation therapy are reduced.

This object is achieved with the device having a plurality of radiation heads arranged in the housing in a fixed manner. The device also having a common radiation source provided for all of the radiation heads, the radiation of which radiation source can be distributed to the radiation heads through a radiation divider, and the radiation source is designed as an electron-radiation source. The device further having at least two diverter elements provided between the radiation divider and each radiation head, and the primary beam and/or the beams strikes the tissue in question lying in at least two planes displaced from one other. The invention distinguishes itself in that a plurality of radiation heads are arranged in a fixed manner in the housing of the device. Through the resting gantry and through the fixed acceleration heads the high technological cost necessary for the precise rotation of the system is avoided. Thus, the initial and operational costs of the apparatus are considerably reduced and the technical reliability significantly increased. Due to the fact that the radiation heads must no longer be rearranged from one radiation direction to the next, waiting times no longer arise.

The possibility arises of equipping each radiation head with its own radiation source. The primary radiation can thus be guided directly to the radiation head in question without the formerly required diversion.

Another variant provides for all of the radiation heads a common radiation source whose radiation can be distributed to the radiation heads. As a starting point, there is accordingly only one primary beam. This arrangement supports the simple and compact construction of the device according to the invention. Furthermore, at least one radiation divider can be provided that distributes the radiation of the radiation source to the individual heads. According to the requirements, this dividing can take place either simultaneously or sequentially. Each radiation head can thus be driven separately or all radiation heads can be driven at the same time.

For guiding the beam at least one diverter element can be provided in the gantry head, which diverter element diverts the radiation of the radiation source and leads it to a radiation head. The diverter elements can be arranged in such a way that they divert the radiation of at least one head for irradiation of the target volume. The diverter element in question can, for example, effect a diversion of the radiation of 90°. A 270° beam diverter, which can be effected with three elements, is advantageous in that the beam guidance effects a double-focusing and this with respect to the beam direction and the beam energy. Through the triple diversion, on the one hand a local focusing improvement is achieved, and on the other hand a sharpening of the energy. The particles which then exit the third diverter element all have essentially the same energy.

It is especially advantageous to have the primary beam and/or the beams impinging on the tissue lie in at least two planes that are displaced from one another. This results in a multiplicity of possibilities with respect to the positioning of the patient as well as the irradiation direction.

The mass of the individual radiation heads can lead to a limitation of possibilities for arrangement in one plane; for this reason, the radiation heads can be arranged in at least two planes that are displaced from one another.

The radiation source can serve as an electron beam source, in which case the electrons in the chain comprising the electron source, the radiation divider, the diverter elements and the radiation head are accelerated, guided, and applicable as the usable radiation. The electrons can also be guided onto a retarding target, so that the electron radiation is converted into hard X-radiation. Here a cylindrical as well as a spherical retarding target can be used.

The beam source can, however, also be a source of protons or heavy nuclei which then can be applied as the usable radiation. The radiation from protons or heavy nuclei can likewise be accelerated and guided in the chain comprising the radiation source, the radiation divider, the diverter element and the radiation head.

For broadening the usable beam, the primary beam can be diverted by means of a scanning device (scanning process). In the case of electrons, these can then be guided again to a retarding target, in order to obtain hard X-radiation. For restriction of the cross section of a beam of energy-rich particles, at least one radiation head can be provided with a multileaf collimator (MLC). In order to realize the intensity-modulated radiation treatment, these mulitleaf collimators can be controllable.

Appropriately, the aperture of the usable beam can be reduced in at least one direction to a small dimension (e.g. millimeters to a few centimeters) in the central plane. This limitation of the aperture of the usable beam is possible either in the transverse direction (crosswise to the longitudinal axis of the patient) and/or in the longitudinal direction (parallel to the longitudinal axis of the patient).

Advantageously, a patient-support table is provided, the movement of which can be controlled according to a radiation plan. By this means, due to the fixed arrangement of the radiation heads, a relative movement can be brought about, so that the necessary dose distribution can be produced.

Here, the patient-support table can be moved according to the radiation plan in a stepwise or continuous manner by means of a digital control. Across from at least one radiation head in the radiation direction on the exit side of the patient can be arranged a radiation detector, in particular a surface radiation detector, which determines both the irradiated contour of the field and the instantaneous dose power as well as the integral applied dose using two-dimensional measurement methodology.

Integrated in the device can be a microprocessor that serves to drive and/or regulate the dynamic components. Thus, by means of the microprocessor the functions of radiation source, radiation divider, radiation guide, sensor device, multileaf collimator, linear table movements and rotational table movements can be driven and/or regulated. With special advantage, the microprocessor can implement the results of a radiation-plan program and control the dynamic components accordingly.

In summary, it is to be remarked that, due to the fact that the present invention can be realized in a simpler manner and has greater technical reliability, the result is a cost-effective alternative to technologies already existing and being further developed.

The present invention is explained in greater detail with the aid of the advantageous embodiment examples represented in the drawings. These show:

FIG. 1: a beam guidance principle according to the present invention

Figure 2:
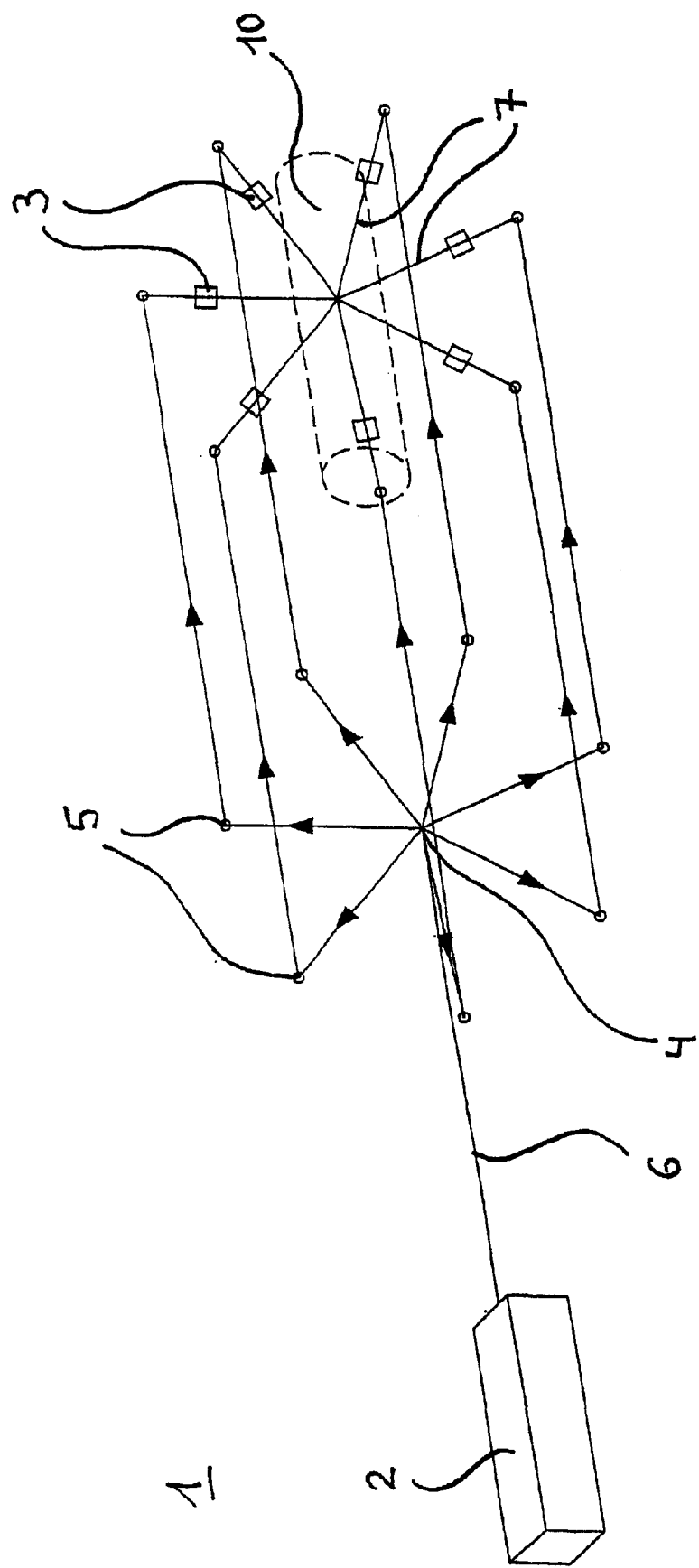

FIG. 2: a spatial representation of the beam guidance principle

Reference numeral 1 indicates the device according to the invention for irradiation of tissue, in its entirety. In particular, the device serves the tumor irradiation of a patient 10 lying on the patient-support table 8. The device 1 displays a radiation source 2, of which the primary beam 6, after several deflections, leads to a radiation head 3. The radiation source 2 as well as the radiation head 3 are arranged in a housing (not shown in the drawings), the radiation emitted from the radiation head 3 striking the tissue of the patient 10. According to the invention a plurality of radiation heads 3 is arranged in a fixed manner in the housing (see FIG. 2). Relative to devices with moving beam-guidance systems, this arrangement has the advantages that apparatus production and operating costs are considerably reduced and that the technical reliability is distinctly increased.

As shown in FIG. 2, a common radiation source 2 is provided for all of the radiation heads 3, the radiation of which source is distributed to the radiation heads 3. However, there also exists the possibility (not shown in the drawings) of equipping each radiation head 3 with a radiation source 2.

If only one radiation source 2 is provided, then at least one radiation divider 4 serves to distribute the radiation of the radiation source 2 to the individual radiation heads 3 or to the diverting elements 5 arranged in between, as the case may be. In the distribution of the radiation, each radiation head 3 can be separately driven or all of the radiation heads 3 simultaneously. The diverting elements 5 serve to steer the radiation of the radiation source 2 and of the beam guide towards the respective radiation head 3.

As shown in the drawings, each diverting element effects a 90° turn of the radiation. The entire diverting of the beam by 270° through three deflections is advantageous because it acts in a double-focusing manner with respect to the beam direction and the beam energy.

The primary beam 6 and the beams 7 striking the tissue lie in planes that are displaced from each other, whereby a multitude of possibilities arises with respect to the supporting of the patient and the radiation directions. Likewise, the radiation heads 3 are arranged in planes that are displaced from each other, so that no spatial arrangement problems due to the mass of the radiation heads 3 arise.

The radiation source 2 depicts an electron-radiation source. The electrons, in the chain radiation source 2, radiation divider 4, diverting elements 5, and radiation head 3, are accelerated, guided, and finally applied as usable radiation. By means of a retarding target (cylindrical or spherical) arranged at the radiation head 3, the electron radiation can be converted into hard X-radiation. The radiation source 2 can, however, also serve as a source for protons or heavy nuclei that are applicable as usable radiation. For broadening the usable beam, the primary beam 6, i.e. the primarily-accelerated charged particles, can be deflected by means of a scanning device 11.

At least one of the radiation heads 3 is equipped with a multileaf collimator 12, which serves to restrict the cross section of the usable beam. For intensity-modulated radiation treatment, the multileaf collimators 12 are controllable.

The aperture of the usable radiation, i.e. the charged particles or the Bremsstrahlung, is limitable in at least one direction to a small dimension in the millimeter to centimeter range in the central plane. This limiting can take place either in the transverse direction (crosswise to the longitudinal axis of the patient) and/or in the longitudinal direction (parallel to the longitudinal axis of the patient).

The movement of the patient-support table 8 can be controlled according to a radiation plan, so that the tissue volume to be treated is completely covered. For this purpose, the patient-support table 8 is movable around at least one rotation axis and/or along its longitudinal axis. The movement can take place continuously or stepwise.

Across from at least one radiation head 3 in the beam direction on the exit side of the patient 10 is arranged a radiation detector 9, in particular a surface radiation detector, by means of which both the irradiated contour of the field and the instantaneous dose power as well as the integral applied dose can be determined through two-dimensional measurement methodology (see FIG. 1).

Further provided in the device 1 is a microprocessor, which is not shown in the drawings. Occurring by means of the microprocessor are the driving and regulating of the collective dynamic components, such as the radiation source 2, the radiation divider 4, the diverting elements 5, etc. The microprocessor also serves to implement the results of a radiation-plan program.

The invention claimed is:

1. A therapeutic device for irradiating a target tissue, the therapeutic device comprising:
   a housing,
   a plurality of radiation heads arranged in the housing in a fixed manner,
   a common radiation source provided for the plurality of radiation heads, wherein the radiation source comprises an electron radiation source and has a primary radiation beam,
   a radiation divider, wherein the primary radiation beam from the common radiation source is distributed to the plurality of radiation heads through the radiation divider, at least two diverter elements provided between the radiation divider and each of the plurality of radiation heads, wherein each of the plurality of radiation heads is positioned relative to each other, and radiation beams released from each of the plurality of radiation heads strike the target tissue, and wherein the plurality of radiation beams lie in at least two planes displaced from one another and electrons are converted into therapeutic X radiation by a retarding target in the radiation heads, wherein at least one radiation head is provided with a multileaf collimator and, a patient-support table, with a controller configured to move the patient-support table in accordance with a therapeutic radiatio plan.

2. The therapeutic device of claim 1, wherein each radiation head is separately controllable.

3. The therapeutic device of claim 1, wherein all of the radiation heads are controllable simultaneously.

4. The therapeutic device of claim 1, wherein each diverter element effects a 90° deflection of the radiation.

5. The therapeutic device of claim 1, wherein the radiation heads are arranged in at least two planes that arc displaced from one another.

6. The therapeutic device of claim 1, wherein the multileaf collimator is controllable in order to realize an intensity-modulated radiation treatment.

7. The therapeutic device of claim 1, wherein an aperture of usable radiation is limitable in at least one direction to a certain dimension in a central plane.

8. The therapeutic device of claim 1, wherein the patient-support table is movable around at least one rotational axis or along a longitudinal axis.

9. The therapeutic device of claim 1, wherein across from at least one radiation head in a radiation direction on an exit side of the patient-support table is arranged a radiation detector.

10. The therapeutic device of claim 9, wherein the radiation detector is a surface radiation detector.

11. The therapeutic device of claim 1, wherein the target tissue is a tumor.

* * * * *